# United States Patent [19]

Bertus et al.

[11] 4,176,140

[45] Nov. 27, 1979

[54] DEHYDROGENATION OF HYDROCARBONS WITH ZINC TITANATE CATALYST

[75] Inventors: Brent J. Bertus; Darrell W. Walker, both of Bartlesville, Okla.

[73] Assignee: Phillips Petroleum Company, Bartlesville, Okla.

[21] Appl. No.: 844,931

[22] Filed: Oct. 27, 1977

Related U.S. Application Data

[63] Continuation-in-part of Ser. No. 743,193, Nov. 19, 1976, abandoned.

[51] Int. Cl.$^2$ .............................................. C07C 11/12
[52] U.S. Cl. .................................... 585/629; 585/661
[58] Field of Search ........................ 260/683.3, 680 R; 252/461

[56] References Cited

U.S. PATENT DOCUMENTS

| | | | |
|---|---|---|---|
| 2,279,198 | 4/1942 | Huppke | 260/683.3 |
| 2,932,673 | 4/1960 | Melik et al. | 260/683.3 |
| 3,308,191 | 3/1967 | Bajars | 260/680 |
| 3,641,182 | 2/1972 | Box et al. | 260/683.3 |
| 3,670,044 | 6/1972 | Drehman et al. | 260/683.3 |
| 3,978,150 | 8/1976 | McWilliams | 260/683.3 |

*Primary Examiner*—Delbert L. Gantz
*Assistant Examiner*—Joseph A. Boska

[57] ABSTRACT

A process is used to dehydrogenate organic compounds to a higher degree of unsaturation by contacting in a first step, the organic compound with a calcined zinc titanate catalyst modified with lithium or magnesium. In the second step, the catalyst is contacted with oxygen essentially in the absence of the dehydrogenatable organic compound. The first and second steps are repeated sequentially.

22 Claims, No Drawings

DEHYDROGENATION OF HYDROCARBONS WITH ZINC TITANATE CATALYST

This application is a continuation-in-part application of Ser. No. 743,193 filed Nov. 19, 1976, now abandoned.

This invention relates to a process for dehydrogenation.

Dehydrogenation processes for the conversion of organic compounds to compounds having a higher degree of unsaturation include both thermal noncatalytic processes and catalytic processes. The former are characterized by undesirable side reactions, low order of conversion and yield and poor product selectivity. The catalytic processes are generally characterized by the particular catalytic material employed and the conditions under which the processes are operated, e.g., in the absence or presence of oxygen. While a number of such catalytic processes have achieved some measure of success, there is a continuing search to develop catalytic materials and processes which exhibit the high activity, high yield of desired product, high selectivity to desired product, longevity and which keep undesirable side reactions to a minimum.

An object of the present invention is to provide a process for the catalytic dehydrogenation of organic compounds in the absence of free oxygen.

Other objects, aspects and advantages of this invention will be readily apparent to those skilled in the art from a reading of the specification and appended claims.

In accordance with the present invention there is provided a process for catalytically dehydrogenating a dehydrogenatable organic compound which process has alternate reaction periods and regeneration periods and comprises contacting an organic compound with a regenerable dehydrogenation catalyst, as described below, in the substantial absence of free oxygen under dehydrogenation conditions for a reaction period; and thereafter passing an oxygen-containing gas in contact with the catalyst under regeneration conditions for a regeneration period.

The process of this invention provides, with respect to known processes for oxidative dehydrogenation of organic compounds, several advantages: The cost of separating and purifying the products of the process of this invention is reduced. Selectivity to the desired product is increased. Less steam is required in the process of this invention.

The dehydrogenation catalyst employed in the process of the present invention is a calcined composition consisting essentially of zinc, titanium, a metal selected from the group consisting of lithium and magnesium, and sufficient oxygen to satisfy the valence requirements of the zinc, titanium and the lithium or magnesium, wherein the atomic ratio of zinc to titanium is in the approximate range of 1.74:1 to 2.15:1, preferably about 2:1, which corresponds to zinc orthotitanate, and the amount of lithium or magnesium ranges from about 0.001 to about 0.5, preferably about 0.005 to 0.2 gram-equivalents of lithium or magnesium per 100 grams of the combined weight of zinc, titanium and oxygen combined therewith.

The catalyst can be prepared by intimately mixing suitable proportions of zinc oxide, titanium dioxide and a suitable compound of lithium or magnesium, and calcining the mixture in air at a temperature in the range of 650° to 1050° C., preferably from 675° to 975° C. It is presently preferred that the titanium dioxide used in preparing the catalyst have an average particle size of less than about 100 millimicrons. Suitable compounds of lithium or magnesium are those compounds which can be calcined to lithium oxide or magnesium oxide, without having undesirable residues in the catalyst, such as, for example, lithium hydroxide, lithium nitrate, lithium acetate, magnesium hydroxide, magnesium nitrate, magnesium acetate and the like.

The catalyst can also be prepared by coprecipitation from aqueous solutions of a zinc compound, a titanium compound and a lithium or magnesium compound. The aqueous solutions are mixed together and the hydroxides are precipitated by the addition of ammonium hydroxide. The precipitate is then washed, dried and calcined, as above. Alternatively, the zinc and titanium can be coprecipitated and the coprecipitate impregnated with a suitable lithium or magnesium compound, then dried and calcined.

The organic feedstocks which can be dehydrogenated in accordance with the present invention are dehydrogenatable organic compounds having from 2 to 12 carbon atoms per molecule and characterized by having at least one

grouping, i.e., adjacent carbon atoms, each having at least one hydrogen atom. Suitable compounds include paraffins, olefins, cycloaliphatics and alkyl aromatic compounds having from 2 to 12 carbon atoms per molecule. Particularly suitable are paraffins and monoolefins, branched or unbranched. Some examples of such applicable hydrocarbon feedstocks are ethane, propane, butane, isobutane, pentane, isopentane, hexane, 2-methylhexane, n-octane, n-dodecane, 1-butene, 2-butene, 2-methyl-butene-1, 2-methyl-butene-2, 2-hexene, 1-octene, 3-methylnonene-4, 1-dodecene, cyclohexane, and the like and mixtures thereof. Particularly appropriate is the conversion of ethane to ethylene, propane to propylene, butanes ro butenes and butadiene, butenes to butadiene, and isopentane to isoamylenes and isoprene.

The process of this invention can be carried out by means of any apparatus whereby there is achieved an alternate contact of the catalyst with the gaseous phase containing the dehydrogenatable organic compound and thereafter of the catalyst with the oxygen-containing gaseous phase, the process being in no way limited to the use of a particular apparatus. The process of this invention can be carried out using a fixed catalyst bed, fluidized catalyst bed or moving catalyst bed. Presently preferred is a fixed catalyst bed.

In order to avoid any casual mixing of the organic compound and oxygen, provision can be made for intermediate supplemental injection of an inert purging gas, such as, for example, nitrogen, carbon dioxide or steam.

The time of reaction, i.e., dehydrogenation, for the dehydrogenatable organic compound can range from about 0.05 second to about 10 minutes, preferably from about 0.1 second to about 5 minutes.

The time of regeneration of the catalyst can range from 1 to 10 times the reaction period.

The temperature of the reaction can range from about 800° to about 1300° F. (426°–705° C.), preferably between 900° and 1200° F. (482°-650° C.), depending upon the nature of the organic feedstock.

The pressure of the reaction can range from about 0.05 to about 250 psia (5 to 1724 kPa).

The organic compound feed rate will generally be in the range of 50 to 5000 volumes of feedstock per volume of catalyst per hour, depending upon the feedstock, and the temperature and pressure employed, preferably from about 100 to about 2500. The presence of steam is frequently beneficial and steam:hydrocarbon molar ratios of up to 50:1 can be used, preferably from about 0.1:1 to about 20:1. An inert gaseous diluent, such as nitrogen or carbon dioxide, can also be used, and if used, will generally be in the same amounts as specified for the steam.

Steam can also be employed in admixture with the oxygen-containing gas during regeneration period. The amount of oxygen, from any source, supplied during the regeneration step will be in an amount sufficient to remove carbonaceous materials from the catalyst. Generally an amount in the range of about 1.5 to 5 times the volume of dehydrogenatable organic compound charged to the dehydrogenation step is employed. The regeneration step is conducted at the same temperature and pressure recited for the dehydrogenation step, although somewhat higher temperatures can be used in some instances.

Thus, the operating cycle will include the successive steps of:

(1) Contacting the organic compound with the catalyst, resulting in the production of more unsaturated compounds. The step is optionally conducted in the additional presence of steam.
(2) Optionally, purging the catalyst with an inert gas.
(3) Contacting the catalyst with free oxygen.
(4) Optionally, purging the catalyst with an inert gas.
(5) Repeating step 1.

The following examples illustrate the invention.

EXAMPLE I

Catalyst Preparation

A series of catalysts was prepared from zinc oxide, titanium dioxide and the metal promoter. Each catalyst was prepared by slurrying 40 g of powdered zinc oxide having an average primary particle size of about 130 microns with 20 grams of titanium dioxide prepared by flame hydrolysis having an average primary particle size of about 30 millimicrons in 300 cc of distilled water in a high speed blender. An aqueous solution of the promoter metal compound, when used, was added to the slurry and blended about 6 minutes. Each mixture was dried overnight in a forced draft oven at 120° C., calcined in air for 3 hours at 1500° F. (816° C.), cooled, ground and sieved to obtain particles of 20-40 mesh in size (U.S. Sieve Series). The promoter metal compounds used, the analyzed concentration of promoter metal found in each catalyst and surface area and apparent bulk density of each catalyst are presented in Table 1.

Table I

| Catalyst Designation | Catalyst Preparation | | | Surface Area, $m^2/g$ | Apparent Bulk Density g/cc |
|---|---|---|---|---|---|
| | Promoter | | | | |
| | Metal Compound | Wt. %[1] | gm-eq.[2] | | |
| A | None | 0 | 0 | 6.5 | 0.96 |
| B | LiOH | 0.07 | 0.01 | 8.0 | 1.02 |
| C | LiOH | 0.16 | 0.02 | 7.9 | 1.17 |
| D | LiOH | 0.36 | 0.05 | 8.2 | 1.18 |
| E | LiOH | 0.68 | 0.10 | 7.4 | 1.23 |
| F | LiOH | 1.08 | 0.16 | 6.8 | 1.35 |
| G | $KNO_3$ | 0.72 | 0.02 | nd[3] | 1.00 |
| H | $Cs_2CO_3$ | 2.4 | 0.02 | nd | 1.04 |
| I | $Mg(NO_3)_2 \cdot 6H_2O$ | 1.5 | 0.03 | nd | 1.09 |
| J | $Mg(NO_3)_2 \cdot 6H_2O$ | 2.5 | 0.05 | 6.1 | 1.05 |
| K | $Ba(NO_3)_2$ | 6.2 | 0.025 | nd | 0.98 |

[1] Analyzed value.
[2] Gram-equivalents per 100 grams of $Zn_2TiO_4$.
[3] Not determined.

EXAMPLE II

Ethane was dehydrogenated at atmospheric pressure in a cyclic manner with each cycle consisting of a 3 minute reaction period, 6 minute regeneration period and 6 minute nitrogen purge flow period. The same temperature was employed for the reaction and regeneration periods. Feed, air and nitrogen were passed to a preheat zone and then to the reactor. A 4 cc sample of each catalyst was charged to a fixed bed automated testing unit and the reactor and catalyst brought up to temperature in the presence of about 250 GHSV nitrogen. Each cycle from this point on consisted of contacting the catalyst with a mixture of nominal 250 GHSV nitrogen and 900 GHSV air for 6 minutes. Air was cut off and nitrogen continued to flow for 6 more minutes to purge air from the system. Ethane, nominal 250 GHSV, was then cut in and allowed to flow for 3 minutes to complete the cycle.

The effluent gas phase, collected from 12 consecutive cycles, was analyzed by means of gas-liquid chromatography for oxygen, nitrogen, ethylene, methane, and carbon oxides. The analyzed values (average of duplicate runs) are shown in Table II along with the reactor temperatures employed. In this and the following examples, the selectivity is based on the gas phase products only and is expressed as the nearest whole number.

Table II

Cyclic Ethane Dehydrogenation

| Run No. | Catalyst Designation | Catalyst Metal/wt. % | Reactor °F. | Temp. °C. | Conversion, Mole % | Product Yields, Mole % Ethylene | Cracked | Carbon Oxides | Selectivity to Ethylene, % | Remarks |
|---|---|---|---|---|---|---|---|---|---|---|
| 1 | A | 0 | 1050 | 566 | 13.1 | 8.8 | 0 | 4.3 | 67 | Control |
| 2 | B | Li/0.07 | 1050 | 566 | 12.9 | 9.8 | 0 | 3.0 | 76 | |
| 3 | C | Li/0.16 | 1050 | 566 | 12.5 | 10.2 | 0.1 | 2.2 | 82 | |
| 4 | D | Li/0.36 | 1050 | 566 | 11.0 | 10.5 | 0 | 0.4 | 96 | |
| 5 | A | 0 | 1150 | 621 | 30.5 | 20.0 | 1.9 | 8.6 | 66 | |
| 6 | B | Li/0.07 | 1150 | 566 | 35.1 | 7.1 | 12.9 | 15.0 | 20 | |
| 7 | C | Li/0.16 | 1150 | 621 | 24.1 | 15.8 | 2.9 | 5.3 | 66 | |
| 8 | D | Li/0.36 | 1150 | 621 | 23.0 | 18.2 | 1.6 | 3.0 | 79 | |

These data show in Runs 2, 3 and 4 and in Runs 6, 7 and 8, at reactor temperatures of 1050° and 1150° F., respectively, that the ethylene yield increases as the lithium promoter level increases from 0.07 wt. % to 0.36 wt. %. At a given promoter level, highest ethylene yields and selectivities to ethylene were obtained at a 1050° F. reactor temperature. The results show that the lithium promoted zinc titanate catalyst is more active for ethane dehydrogenation in a cyclic process at 1050° F. than the unpromoted control as shown in Run 1. At 1150° F., it is necessary to have at least about 0.16 wt. % lithium present to equal or surpass the control catalyst on a selectivity to ethylene basis. The added lithium appears to primarily suppress formation of carbon oxides.

EXAMPLE III

Propane was dehydrogenated at atomspheric pressure with the catalysts of this invention and effluents analyzed in the manner described in Example 2 except that gas phase effluents from 28 consecutive samples were accumulated. Duplicate runs were made. The propane feed rate was 250 GHSV, the nitrogen rate was 250 GHSV and the air rate was 900 GHSV. The effluents were analyzed for oxygen, nitrogen, methane, propane, carbon oxides and propylene. The results are presented in Table III.

At a reactor temperature of 1050° F., the results show the lithium-promoted catalysts to be active for dehydrogenation of propane in a cyclic process but that the unpromoted catalyst is more active. When a reactor temperature of 1150° F. is used, however, the data in runs 8-11 show the beneficial results in increased propylene formation as well as increased selectivity to propylene compared with control Run 7. Run 12 indicates that the highest selectivity to propylene is obtained when the lithium concentration on the catalyst is about 1 weight percent. With this catalyst, the lowest production of carbon oxides, methane and propylene was obtained.

EXAMPLE IV

In another series of tests, n-butane was dehydrogenated with the lithium promoted catalysts. In a closely related series, butene-2 was also dehydrogenated with the lithium promoted catalysts. The cyclic conditions employed were similar to those used in Example III, except that the feed rate was 1000 GHSV and the oxygen rate was 440 GHSV (air 2300 GHSV). The effluent collected from 28 consecutive cycles was analyzed for oxygen, nitrogen, carbon monoxide, carbon dioxide, methane, ethane plus ethylene, propylene, n-butane, butene-1, cis-butene-2, trans-butene-2 and butadiene. The results are presented in Tables IV-A and IV-B.

Table III

Cyclic Propane Dehydrogenation

| Run No. | Catalyst Designation | Li, Wt. % | Reactor °F. | Temp. °C. | Conversion Mole % | Propylene | Carbon Oxides | Methane | Propane | ethylene | Selectivity to Propylene, % | Remarks |
|---|---|---|---|---|---|---|---|---|---|---|---|---|
| 1 | A | 0 | 1050 | 566 | 42.3 | 40.8 | 0.85 | 0 | 57.65 | 0.65 | 96 | Control |
| 2 | B | 0.07 | 1050 | 566 | 40.1 | 38.15 | 0.85 | 0.15 | 60.0 | 1.0 | 95 | |
| 3 | C | 0.16 | 1050 | 566 | 37.0 | 35.65 | 0.60 | 0 | 63.0 | 0.7 | 96 | |
| 4 | D | 0.36 | 1050 | 566 | 30.05 | 28.8 | 0.75 | 0 | 69.9 | 0.55 | 96 | |
| 5 | E | 0.68 | 1050 | 566 | 22.0 | 21.1 | 0.40 | 0 | 78.0 | 0.45 | 96 | |
| 6 | F | 1.08 | 1050 | 566 | 8.9 | 8.35 | 0.15 | 0 | 91.05 | 0.40 | 94 | |
| 7 | A | 0 | 1150 | 621 | 75.05 | 61.6 | 4.45 | 4.4 | 25.0 | 4.1 | 82 | Control |
| 8 | B | 0.07 | 1150 | 621 | 77.9 | 65.1 | 4.65 | 3.85 | 22.1 | 4.35 | 84 | |
| 9 | C | 0.16 | 1150 | 621 | 78.15 | 67.75 | 3.7 | 2.85 | 21.85 | 3.8 | 87 | |
| 10 | D | 0.36 | 1150 | 621 | 77.15 | 67.6 | 3.4 | 2.45 | 22.8 | 3.8 | 88 | |
| 11 | E | 0.68 | 1150 | 621 | 72.7 | 66.0 | 2.25 | 1.5 | 27.35 | 3.0 | 91 | |
| 12 | F | 1.08 | 1150 | 621 | 49.25 | 46.1 | 0.65 | 0.55 | 50.75 | 1.95 | 94 | |

Table IV-A

Cyclic Butane Dehydrogenation

| Run No. | Catalyst Designation | Li, Wt.% | Reactor °F. | Temp. °C. | Conversion Mole % | Butenes | Butadiene | Cracked | Carbon Oxides | Selectivity, % Butenes | Butadiene | Remarks |
|---|---|---|---|---|---|---|---|---|---|---|---|---|
| 1 | A | 0 | 1050 | 566 | 23.6 | 19.0 | 2.9 | 1.4 | 0.3 | 81 | 12 | Control |
| 2 | B | 0.07 | 1050 | 566 | 25.35 | 19.75 | 3.4 | 1.8 | 0.5 | 78 | 13 | |
| 3 | D | 0.36 | 1050 | 566 | 23.5 | 18.0 | 3.5 | 1.5 | 0.4 | 77 | 15 | |
| 4 | E | 0.68 | 1050 | 566 | 18.35 | 13.75 | 2.8 | 1.4 | 0.3 | 75 | 15 | |

Table IV-A-continued

Cyclic Butane Dehydrogenation

| Run No. | Catalyst Designation | Li, Wt.% | Reactor °F. | Temp. °C. | Conversion Mole % | Product Yields, Mole % | | | | Selectivity, % | | Remarks |
| --- | --- | --- | --- | --- | --- | --- | --- | --- | --- | --- | --- | --- |
| | | | | | | Butenes | Butadiene | Cracked | Carbon Oxides | Butenes | Butadiene | |
| 5 | F | 1.08 | 1050 | 566 | 10.2 | 7.5 | 1.45 | 1.05 | 0.2 | 74 | 14 | |
| 6 | A | 0 | 1150 | 621 | 34.2 | 21.55 | 6.55 | 5.65 | 0.5 | 63 | 19 | Control |
| 7 | B | 0.07 | 1150 | 621 | 39.6 | 24.05 | 7.9 | 6.85 | 0.75 | 61 | 20 | |
| 8 | D | 0.36 | 1150 | 621 | 40.2 | 24.55 | 8.35 | 6.5 | 0.7 | 61 | 21 | |
| 9 | E | 0.68 | 1150 | 621 | 35.5 | 21.45 | 7.2 | 6.3 | 0.6 | 60 | 20 | |
| 10 | F | 1.08 | 1150 | 621 | 23.25 | 12.65 | 4.6 | 5.65 | 0.4 | 54 | 20 | |

Table IV-B

Cyclic Butene-2 Dehydrogenation

| Run No. | Catalyst[1] Designation | Li, Wt. % | Reactor ° F. | Temp. ° C. | Conversion Mole % | Product Yields, Mole % | | | Selectivity to Butadiene, % |
| --- | --- | --- | --- | --- | --- | --- | --- | --- | --- |
| | | | | | | Butadiene | Cracked | Carbon Oxides | |
| 1 | A | 0 | 1050 | 566 | 10.8 | 9.9 | 0.2 | 0.2 | 92 |
| 2 | B | 0.07 | 1050 | 566 | 13.1 | 11.7 | 0.35 | 0.45 | 89 |
| 3 | D | 0.36 | 1050 | 566 | 13.85 | 12.3 | 0.5 | 0.4 | 89 |
| 4 | E | 0.68 | 1050 | 566 | 11.95 | 10.7 | 0.35 | 0.4 | 90 |
| 5 | F | 1.08 | 1050 | 566 | 5.55 | 5.0 | 0.05 | 0.2 | 90 |

[1]Catalysts previously used for 56 cycles in butane dehydrogenation, 112 cycles in isobutane dehydrogenation and 56 cycles in butene-2 dehydrogenation.

The cyclic butane dehydrogenation results shown in Table IV-A indicate that the lithium-promoted catalysts inprove selectivity to butadiene with concomittant decrease in selectivity to butenes compared to the control Runs 1 and 6 at both 1050° F. and 1150° F. reactor temperatures. In general, the catalysts containing from about 0.05 to about 0.7 weight percent lithium, in Runs 2, 3, 4 and 8, 9, 10, also yield more butadiene than the control catalysts under the conditions employed.

The cyclic butene-2 dehydrogenation results, in general, parallel those obtained with n-butane with respect to increased production of butadiene. The selectivities to butadiene, however, are slightly lower than that shown by the control catalyst. It is noteworthy that the catalysts used in the butene-2 dehydrogenation had been previously employed for 224 cycles in n-butane, isobutane and butene-2 dehydrogenation studies before the results shown in Table IV-B were obtained.

EXAMPLE V

In a series of runs, isopentane was dehydrogenated with each catalyst shown in Table I. The cyclic conditions employed were similar to those used in Example III. The effluent collected from 29 consecutive cycles were analyzed for oxygen, nitrogen, carbon monoxide, carbon dioxide, methane, ethane plus ethylene, propylene, butene-1, cis-butene-2, trans-butene-2, isopentane, n-pentane, 3-methylbutene-1, 2-methylbutene-1, pentene-1, 3-methylbutene-2, isoprene and trans-piperylene. The conditions employed and results obtained are summarized in Table V. The reactor temperature employed in each run was 1050° F.

Table V

Cyclic Isopentane Dehydrogenation

| Run No. | Catalyst Designation | Metal/Wt. % | Conversion Mole % | Product Yields, Mole % | | | | Selectivity, % | | Remarks |
| --- | --- | --- | --- | --- | --- | --- | --- | --- | --- | --- |
| | | | | Isoamylene | Isoprene | Cracked | Carbon Oxides | Isoamylene | Isoprene | |
| 1 | A | 0 | 43.35 | 28.25 | 11.45 | 2.55 | 1.1 | 65 | 26 | Control |
| 2 | B | Li/0.07 | 46.7 | 31.3 | 11.3 | 2.75 | 1.0 | 67 | 24 | |
| 3 | C | Li/0.16 | 52.55 | 35.55 | 11.5 | 2.8 | 1.0 | 68 | 22 | |
| 4 | D | Li/0.36 | 49.65 | 33.7 | 11.5 | 2.7 | 1.05 | 68 | 23 | |
| 5 | E | Li/0.68 | 48.35 | 32.1 | 13.2 | 2.35 | 0.7 | 66 | 27 | |
| 6 | F | Li/1.08 | 33.75 | 22.4 | 9.45 | 1.35 | 0.5 | 66 | 28 | |
| 7 | G | K/0.72 | 1.65 | 0 | 0 | 1.5 | 0.2 | 0 | 0 | |
| 8 | G | K/0.72 | 1.75 | 0 | 0 | 1.6 | 0.2 | 0 | 0 | |
| 9 | H | Cs/2.4 | 1.95 | 0 | 0 | 1.5 | 0.3 | 0 | 0 | |
| 10 | H | Cs/2.4 | 2.15 | 0 | 0 | 1.8 | 0.3 | 0 | 0 | |
| 11 | K | Ba/6.2 | 4.55 | 1.9 | 1.4 | 1.25 | 0 | 42 | 31 | |
| 12 | K | Ba/6.2 | 4.0 | 2.15 | 0.7 | 1.15 | 0 | 54 | 18 | |
| 13 | I | Mg/1.5 | 41.1 | 26.95 | 11.2 | 2.1 | 0.8 | 66 | 27 | |
| 14 | J | Mg/2.5 | 40.95 | 28.05 | 10.0 | 2.15 | 0.8 | 68 | 24 | |
| 15 | I | Mg/1.5 | 44.65 | 29.45 | 12.15 | 2.15 | 0.85 | 66 | 27 | |
| 16 | J | Mg/2.5 | 45.5 | 31.15 | 11.15 | 2.35 | 0.9 | 68 | 25 | |

The results presented in Table V demonstrate that the lithium promoted catalysts are active in isopentene dehydrogenation under the cyclic conditions employed. The data show the catalysts containing from about 0.07-0.68 weight percent lithium generally produce more isoamylenes and about the same amount of isoprene as does the control catalyst. The catalyst of Run 5 (0.68 weight percent lithium), however, produces more isoamylenes and isoprene than all the catalysts tested. The invention catalyst containing about 1.08 weight percent lithium, Run 6, is less active in producing the desired products (as shown in other Examples)

but generally has a somewhat higher selectivity to these products than does the control catalyst.

The results presented in Runs 7-12 show that promotion of zinc titanate with potassium or cesium is not equivalent to lithium promotion since the catalysts are inactive under the conditions employed.

The results shown in Runs 13-16 with the magnesium-promoted catalysts show that selectivity to isoamylenes and/or isoprene is slightly higher than that obtained with the unpromoted catalyst. The yields of those products obtained are slightly lower with the magnesium-promoted catalysts than with the control catalyst. Runs 11 and 12 show that barium promotion is not equivalent to magnesium promotion since the barium-containing catalyst is inactive under the process conditions employed.

Resonable variations and modifications, which will be apparent to those skilled in the art, can be made in this invention without departing from the spirit and scope thereof.

We claim:

1. A process for catalytically dehydrogenating a dehydrogenatable hydrocarbon feedstock having at least one

grouping which comprises: contacting said feedstock with a regnerable dehydrogenation catalyst in the substantial absence of free oxygen under dehydrogenation conditions wherein said regenerable dehydrogenation catalyst is prepared by calcining a mixture of zinc oxide and titanium dioxide and a metal selected from the group consisting of lithium and magnesium at a temperature in the range of from about 650° to about 1050° C.

2. A process according to claim 1 wherein said catalyst consists essentially of zinc, titanium, a metal selected from the group consisting of lithium and magnesium, and combined oxygen.

3. A process according to claim 2 wherein the atomic ratio of zinc to titanium in said catalyst is in the approximate range of 1.74:1 to 2.15:1 and the amount of oxygen is sufficient to satisfy the valence requirements of said zinc, said titanium, and said lithium or said magnesium and the amount of said lithium or said magnesium is in the approximate range of 0.001 to 0.5 gram-equivalent per 100 grams of the combined weight of said zinc, said titanium and said combined oxygen.

4. A process according to claim 1 wherein said dehydrogenatable hydrocarbon feedstock is contacted with said catalyst under dehydrogenation conditions for a reaction period in the range of about 0.05 second to 10 minutes.

5. A process according to claim 1 wherein following the reaction period of said dehydrogenatable hydrocarbon feedstock with said regenerable dehydrogenation catalyst, said catalyst is thereafter regenerated by contacting said catalyst with an oxygen-containing gas under regeneration conditions.

6. A process according to claim 5 wherein said catalyst is contacted for a regeneration period ranging from about 1 to 10 times the length of the dehydrogenation period.

7. A process according to claim 5 wherein steam is additionally present in admixture with said oxygen-containing gas during regeneration.

8. The process according to claim 1 wherein said feedstock is a dehydrogenatable hydrocarbon having 2 to 12 carbon atoms per molecule.

9. A process according to claim 1 wherein said catalyst is zinc orthotitanate containing from about 0.005 to about 0.2 gram-equivalent of said lithium per 100 grams of said zinc orthotitanate.

10. A process according to claim 1 wherein the reaction temperature is in the range of about 426° to 705° C.

11. A process according to claim 1 wherein the pressure is between 0.05 and 250 psia.

12. A process according to claim 1 wherein said reaction period is in the approximate range of about 0.1 second to 5 minutes.

13. A process according to claim 5 further comprising the intermediate step of purging said catalyst after regeneration with an inert gas befoe reuse thereof for the dehydrogenation of said dehydrogenatable hydrocarbon feedstock.

14. A process according to claim 1 wherein said catalyst is calcined at a temperature in the approximate range of 675° to 975° C.

15. A process according to claim 1 wherein said titanium dioxide has an average particle size of less than 100 millimicrons.

16. A process according to claim 1 wherein said titanium dioxide has an average particle size of about 30 millimicrons.

17. The process according to claim 1 wherein said feedstock is isopentane.

18. The process according to claim 1 wherein said feestock is propane.

19. The process according to claim 1 wherein said feedstock is ethane.

20. The process according to claim 1 wherein said feedstock is n-butane.

21. The process according to claim 1 wherein said feedstock is butene-2.

22. The process of claim 1 wherein said catalyst is prepared by calcining a miture of zinc oxide, titanium doixide and lithium hydroxide at a temperature in the range of about 650° to about 1050° C.

* * * * *

UNITED STATES PATENT AND TRADEMARK OFFICE
CERTIFICATE OF CORRECTION

PATENT NO. : 4,176,140

DATED : November 27, 1979

INVENTOR(S) : Brent J. Bertus and Darrell W. Walker

It is certified that error appears in the above-identified patent and that said Letters Patent are hereby corrected as shown below:

Column 9, line 34, "regnerable" should be --- regenerable ---.

Column 10, line 32, "befoe" should be --- before ---.

Column 10, line 55, "miture" should be --- mixture ---.

Signed and Sealed this

Fifth Day of August 1980

[SEAL]

Attest:

SIDNEY A. DIAMOND

Attesting Officer

Commissioner of Patents and Trademarks